(12) United States Patent
Paul et al.

(10) Patent No.: US 8,940,925 B2
(45) Date of Patent: Jan. 27, 2015

(54) METHOD FOR PURIFYING THE AZEOTROPIC FRACTION GENERATED DURING THE SYNTHESIS OF N,N-DIMETHYL AMINOETHYL ACRYLATE

(75) Inventors: Jean-Michel Paul, Metz (FR); Coralie Graire, Porcelette (FR); Audrey Riehl, Ternay (FR)

(73) Assignee: Arkema France, Colombes (FR)

( * ) Notice: Subject to any disclaimer, the term of this patent is extended or adjusted under 35 U.S.C. 154(b) by 853 days.

(21) Appl. No.: 13/146,601

(22) PCT Filed: Jan. 27, 2010

(86) PCT No.: PCT/FR2010/050119
§ 371 (c)(1),
(2), (4) Date: Sep. 22, 2011

(87) PCT Pub. No.: WO2010/086547
PCT Pub. Date: Aug. 5, 2010

(65) Prior Publication Data
US 2012/0035389 A1    Feb. 9, 2012

(30) Foreign Application Priority Data

Jan. 27, 2009  (FR) ...................................... 09 50471

(51) Int. Cl.
*C07C 213/06* (2006.01)
*C07C 231/10* (2006.01)
*C07C 213/10* (2006.01)

(52) U.S. Cl.
CPC .................................... *C07C 213/10* (2013.01)
USPC ........................................... 560/218; 560/217

(58) Field of Classification Search
CPC ............................ C07C 213/06; C07C 213/10
USPC .................................................. 560/218, 217
See application file for complete search history.

(56) References Cited

U.S. PATENT DOCUMENTS

2004/0171868 A1 *   9/2004   Geisendoerfer et al. ...... 560/217

FOREIGN PATENT DOCUMENTS

| EP | 0906902 | 4/1999 |
|---|---|---|
| FR | 2811986 | 12/2002 |

* cited by examiner

Primary Examiner — Yevegeny Valenrod
(74) Attorney, Agent, or Firm — Hunton & Williams LLP

(57) ABSTRACT

The invention relates to a method for producing N,N-dimethylaminoethyl acrylate by the transesterification reaction of an alykl acrylate by N1N-dimethylaminoethanol, and more particularly relates to a method for purifying the azeotropic fraction generated during said reaction, thereby enabling the recycling thereof on the alkyl acrylate production unit. The aim of the method of the invention is in particular to remove the acetaldehyde and the dialkoxyethane contained in the azeotropic fraction, either by the direct distillation of the azeotropic fraction or by the distillation of the aqueous phase resulting from the water scrubbing of the azeotropic fraction.

11 Claims, 2 Drawing Sheets

METHOD FOR PURIFYING THE AZEOTROPIC FRACTION GENERATED DURING THE SYNTHESIS OF N,N-DIMETHYL AMINOETHYL ACRYLATE

CROSS-REFERENCE TO RELATED APPLICATIONS

This application is the U.S. National Phase of International Application No. PCT/FR2010/050119 filed on Jan. 27, 2010, which claims priority to French Application No. FR 0950471 filed Jan. 27, 2009, both of which are incorporated by reference herein in their entireties.

FIELD OF THE INVENTION

The present invention relates to the production of N,N-dimethyl aminoethyl acrylate by the transesterification reaction of an alkyl acrylate by N,N-dimethyl aminoethanol, and more particularly relates to a method for purifying the azeotropic fraction generated during said reaction, enabling the recycling thereof to the alkyl acrylate production unit.

N,N-Dimethyl aminoethyl acrylate (called DMAEA hereinafter) corresponding to formula (I):

BACKGROUND

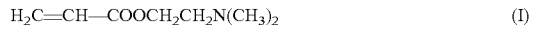

$$H_2C=CH-COOCH_2CH_2N(CH_3)_2 \quad (I)$$

is obtained by the transesterification reaction between a lower alkyl acrylate of formula (II): $CH_2=CH-COOR_1$ in which $R_1$ represents the methyl or ethyl radical, and N,N-dimethyl aminoethanol (DMAE), according to the following reaction scheme:

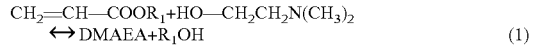

$$CH_2=CH-COOR_1 + HO-CH_2CH_2N(CH_3)_2$$
$$\leftrightarrow DMAEA + R_1OH \quad (1)$$

The reaction is generally carried out in the presence of an excess of lower alkyl acrylate and the reaction is displaced towards formation of DMAEA by distilling the lower alcohol $R_1OH$ in the form of a lower acrylate/$R_1OH$ alcohol azeotrope, which can advantageously be recycled, if its quality permits, to the lower acrylate production unit, said lower acrylate being produced by direct esterification of acrylic acid with the alcohol $R_1OH$.

According to document EP 906 902, the azeotropic mixture resulting from distillation is purified on an ion-exchange resin, thus reducing its content of nitrogen associated with the presence of aminated by-products that may form during the transesterification reaction.

During synthesis of DMAEA by the transesterification reaction, there is generally formation of acetaldehyde $CH_3CHO$ as by-product. The acetaldehyde can then react with the alcohol $R_1OH$ to give an acetal, dialkoxyethane, according to the reaction:

$$CH_3CHO + 2R_1OH \leftrightarrow CH_3CH(OR_1)_2 + H_2O \quad (2)$$

The dialkoxyethane is dimethoxyethane or diethoxyethane depending on whether the DMAEA is prepared from methyl acrylate, or from ethyl acrylate.

The acetaldehyde and dialkoxyethane produced during the synthesis of DMAEA are predominantly in the lower acrylate/$R_1OH$ alcohol azeotropic fraction, thus contributing to contamination thereof.

During recycling of the azeotropic fraction to the production unit for methyl acrylate or ethyl acrylate, the acetaldehyde, on coming into contact with the methanol or ethanol and the acid catalyst that are present for effecting the esterification reaction, is transformed to dialkoxyethane, which is added to the dialkoxyethane already present in the recycled azeotropic fraction. The result is production of methyl acrylate or ethyl acrylate heavily contaminated with dialkoxyethane. This applies in particular to ethyl acrylate, since diethoxyethane has a boiling point of the same order as that of ethyl acrylate.

There is therefore a need to find a method for eliminating some or all of the acetaldehyde and of the dialkoxyethane present in the azeotropic fraction generated during the synthesis of N,N-dimethyl aminoethyl acrylate from a lower acrylate, said fraction being recyclable to the lower acrylate production unit, otherwise the lower acrylate will be heavily contaminated with dialkoxyethane. Purification of the lower acrylate proves difficult, as the difference between the boiling point of the lower acrylate and that of the dialkoxyethane is relatively small.

Accordingly, it is difficult to produce an alkyl acrylate free from dialkoxyethane, if acrylate/alcohol fractions containing it or which contain its precursor acetaldehyde, are recycled to the alkyl acrylate production unit.

Elimination of acetaldehyde from the lower acrylate/alcohol fractions by simple reduction using a reducing agent for example of the type $NaBH_4$, $LiAlH_4$, sodium sulfite, is not conceivable in the present case. In fact, in the presence of lower acrylate, use of these reducing agents would lead to the formation of large amounts of Michael adducts (methyl methoxypropionate or ethyl ethoxypropionate). This would be reflected in a loss of alkyl acrylate and of lower alcohol (methanol or ethanol).

SUMMARY OF THE INVENTION

One of the objectives of the present invention is therefore to be able to provide problem-free recycling, to the alkyl acrylate production unit, of the alkyl acrylate/alcohol fraction generated in the form of azeotrope during the synthesis of DMAEA, the recycling of this fraction being an economic necessity.

Another objective of the present invention is to prevent the acetaldehyde present in the azeotropic fraction received from the synthesis of DMAEA from generating dialkoxyethane in the alkyl acrylate production unit, which would be added to the dialkoxyethane already present in the azeotropic fraction.

The present invention relates to a method for purifying the azeotropic fraction generated during the synthesis of DMAEA that is particularly suitable for the recycling of this fraction in an alkyl acrylate synthesis process, and only requiring a moderate number of steps.

DETAILED DESCRIPTION OF PREFERRED EMBODIMENTS

Figure 1:
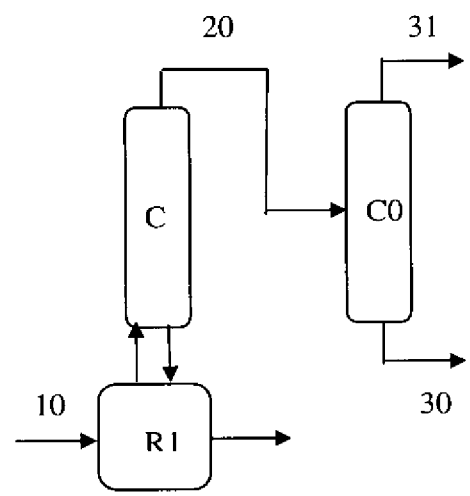
FIG. 1 is a schematic representation of a method according to the present invention comprising distilling transesterification reactor to yield an alkyl acrylate/lower alcohol azeotropic fraction and then distilling the azeotropic fraction in a second distillation column.

The present invention relates to a method for purifying the azeotropic fraction generated during the synthesis of N,N-dimethyl aminoethyl acrylate of formula (I):

$$H_2C=CHCOOCH_2CH_2N(CH_3)_2 \quad (I)$$

by transesterification of an alkyl acrylate of formula (II) $CH_2=CH-COOR_1$ with $R_1$ representing the methyl or ethyl radical, by N,N-dimethyl aminoethanol, said azeotropic fraction comprising alkyl acrylate (II), the lower alcohol $R_1OH$ formed during the reaction, and by-products such as acetaldehyde and dialkoxyethane of formula (III) $CH_3-CH(OR_1)_2$ being distilled by means of a first distillation column mounted above the transesterification reactor, characterized in that said fraction is distilled by means of a second distillation column for separating the by-products acetaldehyde and dialkoxyethane, the minority acetaldehyde-rich overhead product, containing alkyl acrylate (II), lower alcohol $R_1OH$, most of the acetaldehyde and traces of dialkoxyethane, being removed, while the main bottom product with low acetaldehyde content, containing alkyl acrylate (II), lower alcohol $R_1OH$, most of the dialkoxyethane (II) and traces of acetaldehyde, is recycled in an alkyl acrylate synthesis process (II) by reaction of acrylic acid and lower alcohol $R_1OH$.

According to a variant of the method according to the invention, distillation of the azeotropic fraction for separating the by-products acetaldehyde and dialkoxyethane is carried out directly in the first distillation column mounted above the transesterification reactor, the minor acetaldehyde-rich fraction, containing alkyl acrylate (II), lower alcohol $R_1OH$, most of the acetaldehyde and traces of dialkoxyethane, being removed at the top, while the main fraction with low acetaldehyde content, containing alkyl acrylate (II), lower alcohol $R_1OH$, most of the dialkoxyethane (II) and traces of acetaldehyde, is extracted via a side stream from said first column.

During the synthesis of DMAEA by transesterification of methyl acrylate (or of ethyl acrylate), an azeotropic fraction comprising methyl acrylate (or ethyl acrylate), methanol (or ethanol) and that may generally contain from 100 ppm to 1000 ppm of acetaldehyde and from 100 ppm to 1000 ppm of dialkoxyethane (dimethoxyethane or diethoxyethane respectively), is distilled, during the reaction phase, by means of a distillation column mounted above the transesterification reactor.

Depending on the efficiency of the column used and the distillation conditions, this fraction generally contains from 35% to 54% of methanol or from 60% to 72% of ethanol.

According to the first variant of the invention, the method aims only to eliminate the acetaldehyde present in the azeotropic fraction, which is easily the main contributor to the subsequent formation of dialkoxyethane, during recycling of the azeotropic fraction in the production unit for methyl acrylate or ethyl acrylate.

In this case, the distillation conditions are adjusted so as to remove all of the acetaldehyde, or at least 90%, at the column top, while minimizing the losses of lower acrylate and of lower alcohol in this acetaldehyde-rich overhead stream.

It is possible to use a column with simple packing such as Pall rings, or structured of the Multiknit type or any other type of column. Column efficiency must be greater than 10 and advantageously the distillation column comprises from 10 to 20 theoretical plates, preferably from 12 to 18 theoretical plates. The distillation column is surmounted by a condenser supplied with a heat-transfer fluid heated to a temperature in the range from 20° C. to 50° C., preferably from 25° C. to 35° C. The column can operate from atmospheric pressure to 2 bar, preferably at atmospheric pressure.

Generally at least one polymerization inhibitor, selected for example from phenolic inhibitors (hydroquinone, hydroquinone methyl ether, di-tert-butyl paracresol etc.), phenothiazine, the TEMPO nitroxyl compounds of type 4-OH or 4-oxo TEMPO, etc., is added at a rate of 100 to 5000 ppm to the azeotrope to be distilled.

Bubbling with air or with low-oxygen air (7% $O_2$ by volume) is advantageously introduced in the column to reinforce the action of the polymerization inhibitors.

The azeotropic fraction depleted of acetaldehyde is recovered at the bottom of the second distillation column, or can be recovered via a side stream directly from the first column for distillation of the alkyl acrylate/alcohol azeotrope of the DMAEA production unit. This fraction, which can no longer generate dialkoxyethane, can advantageously be recycled.

Figure 2:
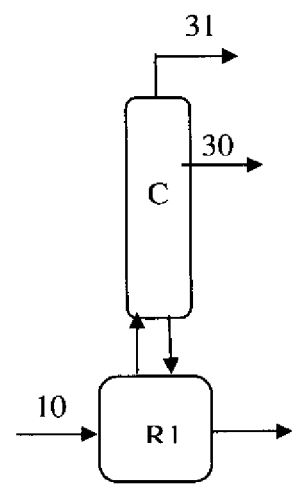
FIG. 2 is a schematic representation of a method according to the present invention comprising distilling the azeotropic fraction directliy in a column in communication with the transesterification reactor.

This variant of the invention can be illustrated according to the 2 configurations in the accompanying FIGS. 1 and 2.

According to the configuration in FIG. 1, the transesterification reactor R1, supplied with the reactants 10 (alkyl acrylate and DMAE), is surmounted by a first distillation column C for continuously removing, at the top, the alkyl acrylate/lower alcohol azeotropic fraction 20 generated during the transesterification reaction. According to the invention, said fraction 20 is distilled in a second distillation column C0, from which an acetaldehyde-rich fraction 31 is extracted at the top, and a purified azeotropic fraction 30 at the bottom. Column C0 generally comprises from 10 to 20 theoretical plates (not including condenser and boiler), feed generally taking place between plates 3 and 10, counting from the top of the column (not counting the condenser).

According to the configuration in FIG. 2, the distillation of acetaldehyde is carried out directly in the first column C situated above the transesterification reactor R1. It is not necessary to add the second distillation column, by adapting the distillation conditions of column C, notably a number of theoretical plates in the range from 12 to 18, and by adding a side-stream line in the top half of the column, for example at level 6 or 7 in the case of a column with 15 plates. The acetaldehyde-rich fraction 31 leaves at the top of column C, whereas the purified alkyl acrylate/lower alcohol azeotropic mixture 30 is drawn off via this side stream of said column C.

The operating conditions of distillation columns C and C0 will be adapted by a person skilled in the art to remove of the order of 90% of the acetaldehyde present in the azeotropic fraction and to limit the losses of lower acrylate and lower alcohol.

The purified azeotropic fraction 30 is then advantageously recycled to the alkyl acrylate production unit.

According to a second variant of the invention, the method aims to degrade the dialkoxyethane to acetaldehyde, then remove the latter by distillation. The result is an azeotropic fraction depleted both of acetaldehyde and of dialkoxyethane.

Shifting the equilibrium of acetalization towards formation of acetaldehyde is effected in the presence of water and an acid catalyst, by distilling the acetaldehyde as it is formed.

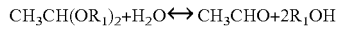

$$CH_3CH(OR_1)_2 + H_2O \leftrightarrow CH_3CHO + 2R_1OH$$

This reaction is known, but its application within the scope of purification of the azeotropic fraction generated by the synthesis of DMAEA has never been described in the prior art.

According to this second variant, at least one polymerization inhibitor, selected for example from phenolic inhibitors (hydroquinone, hydroquinone methyl ether, di-tert-butyl paracresol etc.), phenothiazine, TEMPO nitroxyl compounds of the type 4-OH or 4-oxo TEMPO, etc., are added at a rate of 100 to 5000 ppm to the azeotropic fraction. Then from 3 to 20 wt. % of water is added to this mixture; the amount of water added is preferably between 5 and 10 wt. % relative to the final mixture.

An acid catalyst is also added; among the acid catalysts, we may mention mineral acids such as sulfuric acid, hydrochloric acid, phosphoric acid, sulfonic acids such as methanesulfonic acid or para-toluenesulfonic acid, sulfonated cationic resins, or strongly acidic zeolites.

The strong cationic resins in the form of gel or macroporous are preferred as acid catalyst, as they are easier to use.

The catalyst can be used at a rate from 5 to 20 wt. % relative to the amount of azeotropic fraction to be treated. From 10 to 15 wt. % of a strong cationic resin is preferably used.

The amount of catalyst employed can be less than 5% at the expense of the degree of reduction of the dialkoxyethane, or greater than 20% without giving a notable advantage.

Among the cationic resins that can be used, we may mention for example the resins Amberlyst 15, Lewatit K2620 or K1461, Diaion PK228.

The catalyst can be brought in contact with the azeotropic fraction to be treated in a mechanically stirred reactor, heated by means of a double jacket in which a thermostatically controlled fluid circulates, on a multistage bed of resin recirculated on an external reboiler, on a cartridge of resin fed in the ascending or descending direction and placed on a recirculating loop of a reactor, or in a reactive column.

The method can be carried out in batch mode or continuously.

The continuous removal of acetaldehyde is carried out via a distillation column, for example a plate column, a column with random or structured packing.

Bubbling with air or low-oxygen air (8% $O_2$ by volume) is advantageously introduced in the mixture throughout operation to reinforce the action of the polymerization inhibitors.

The distillation column is surmounted by a condenser supplied with a heat-transfer fluid heated to a temperature in the range from 20° C. to 50° C.

The uncondensed vapors, rich in acetaldehyde, also contain lower acrylate and alcohol. They are then condensed by means of a cold trap. The degree of recovery of acetaldehyde in this overhead product is generally above 95%. The losses of lower acrylate (methyl acrylate or ethyl acrylate) and of alcohol (methanol or ethanol) in this fraction depend on the distillation conditions (column efficiency, operating conditions), and are generally low when employing distillation in the conditions described previously.

This acetaldehyde-rich fraction is removed and must be minimized as it may be accompanied by a loss of lower ester and lower alcohol.

The lower acrylate/lower alcohol mixture from which some or all of the acetaldehyde and dialkoxyethane has been removed can then be recycled to the production unit for lower acrylate without risk of contaminating the latter.

According to a third variant of the invention, the method aims firstly to extract, with water, the lower alcohol and the acetaldehyde present in the azeotropic fraction, and then carry out distillation on the aqueous fraction received from washing with water. This washing with water is carried out on a column for extraction with water C1 fed in countercurrent.

The extraction column C1 receives the azeotropic fraction at the bottom and water at the top. The lower acrylate from which lower alcohol and acetaldehyde have been removed is recovered at the top. Various types of extraction columns can be used. As an example, it is possible to use a compartmented column comprising a rotating shaft with a rotary disk in the middle of each compartment, which provides excellent contact between the phases.

The extraction column C1 can be independent of the lower acrylates unit or it can be a column of type C1 already integrated into the plant for production of lower acrylates.

At the top of extraction column C1, we obtain a fraction containing essentially alkyl acrylate (II) and a variable amount of dialkoxyethane, which can be recycled advantageously to the transesterification reaction, and at the bottom of extraction column C1 we obtain an aqueous fraction containing most of the water that was used for washing, the lower alcohol and acetaldehyde, which, after distillation, leads on the one hand, at the bottom of the distillation column, to a main aqueous fraction depleted of acetaldehyde and rich in lower alcohol, and said fraction can then be recycled directly to the reaction step between acrylic acid and lower alcohol in an alkyl acrylate synthesis process, and on the other hand to an overhead product from the distillation column containing most of the acetaldehyde, which is then removed.

Advantageously, the dialkoxyethane present in the azeotropic fraction can be transformed to acetaldehyde, in the presence of water and an acid catalyst, as described previously, prior to extraction of the lower alcohol with water, thus leading finally to a fraction free from dialkoxyethane.

Advantageously, distillation of the aqueous fraction containing the lower alcohol and acetaldehyde obtained at the bottom of extraction column C1 is carried out by means of two successive columns, the first column C2 serving for separating the water that is recovered at the bottom of column C2 and which is either removed, or recycled to the extraction column C1, and the overhead product from column C2 comprising alcohol and acetaldehyde is then sent to a second distillation column C3, for separating a bottom product composed principally of acetaldehyde-free alcohol, which can be recycled for the reaction step with acrylic acid, and an acetaldehyde-rich overhead product, which will be destroyed. A particular embodiment of this variant of the method consists of recycling the bottom product of column C3, composed principally of alcohol and free from acetaldehyde, partly for the reaction step with acrylic acid and partly at the top of column C2.

Another particular embodiment of this variant of the method consists of returning most of the overhead product of column C3, which contains acetaldehyde, to reflux on column C3, the residue of the stream being purged in order to lower the concentration of acetaldehyde in the plant.

Figure 3:
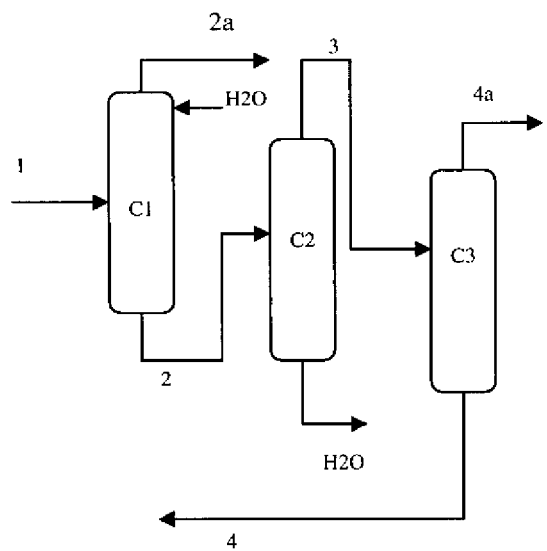
FIG. 3 is a schematic representation of a method according to the present invention wherein the azeotropic fraction is treated with water in the presence of an catalyst to convert the dialkoxyethane to acetaldehyde and lower alcohol, and the acetaldehyde is distilled as it forms.
Figure 4:
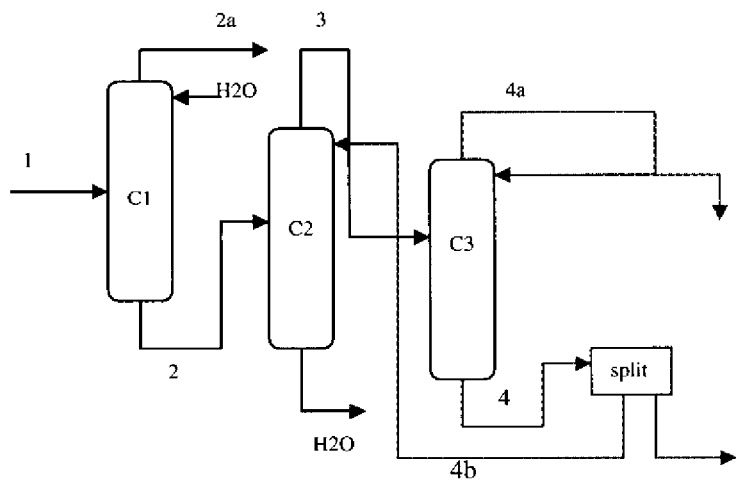
FIG. 4 is a schematic representation of a method according to the present invention wherein the azeotropic fraction is treated with water in the presence of an acid catalyst to convert the dislkoxyethane to acetaldehyde and lower alcohol, and the acetaldehyde is distilled as it forms, wherein most of the overahead product of column C3, which contains acetsldehyde, is returned in reflux to that column and the effluent at the bottom of column C3, depleted of acetaldehyde, is returned partly to the top of column C2 and partly to the reation zone.

This variant of the invention can be illustrated according to the two configurations in the accompanying FIGS. 3 and 4.

According to the configuration in FIG. 3, the azeotropic fraction 1 containing lower acrylate, alcohol, acetaldehyde and a variable amount of dialkoxyethane is washed with water in a column C1 which may or may not be integrated in the lower acrylates unit, from the top of which a stream 2a essentially comprising lower acrylate is withdrawn. Stream 2, depleted of lower acrylate and containing all of the acetaldehyde, is sent to a first distillation column C2, from which water is separated at the bottom and a fraction 3 constituted essentially of alcohol and acetaldehyde. This fraction 3 is sent to a distillation column C3, which removes all of the acetaldehyde contained in stream 3. The effluent 4 from the bottom of column C3, from which the acetaldehyde has been removed, is returned to the reaction zone for producing alkyl acrylate. Formation of dialkoxyethane in the reaction zone is accordingly reduced, which makes it possible to limit the dialkoxyethane content of the alkyl acrylate produced. The acetaldehyde-rich stream 4a is removed, leading to an inevitable loss of lower ester and lower alcohol.

According to the configuration in FIG. 4, stream 4a from the top of column C3 is distributed in such a way that most of the stream is returned in reflux to column C3; the rest of the stream is purged in order to lower the concentration of acetaldehyde in the plant. The effluent 4 at the bottom of column C3, depleted of acetaldehyde, is returned partly to the top of column C2 (stream 4b) and partly to the reaction zone. By operating according to the configuration in FIG. 4, the concentration of acetaldehyde in the leakage from column C3 is greatly increased and accordingly the losses of reactants (lower alcohol/lower ester) are reduced owing to the compulsory destruction of this fraction.

Advantageously, the third variant of the method of the invention is carried out directly on the production unit for lower alkyl acrylate, in the step for purification of raw acrylate from the acrylic acid/lower alcohol reaction mixture. This has the advantage that the azeotropic fraction is not treated separately, and special equipment is not required for said treatment. The azeotropic fraction received from production of DMAEA is recycled directly to the column for extraction with water C1 of the light acrylates production unit; removal of the acetaldehyde supplied by this fraction, recycling of the alcohol present in this fraction and recovery of the alkyl acrylate also present in this fraction can be performed at the same time as purification of the raw acrylate obtained from the reaction mixture. For this, the azeotropic fraction is fed into a liquid/liquid extraction column supplied with water, just like the raw reaction mixture after prior removal of a part of the water of the reaction, the heavy compounds and the residual acrylic acid.

The invention also relates to a method of synthesis of N,N-dimethyl aminoethyl acrylate of formula (I):

$$H_2C=CHCOOCH_2CH_2N(CH_3)_2 \quad (I)$$

by transesterification of an alkyl acrylate of formula (II) $CH_2=CH-COOR_1$ with $R_1$ representing the methyl or ethyl radical, by N,N-dimethyl aminoethanol, employing a step of purification of the azeotropic fraction generated during the reaction, according to the different variants defined previously, permitting recycling of said fraction to the alkyl acrylate production unit.

The following examples illustrate the present invention but without limiting its scope.

EXAMPLES

The percentages are expressed as percentages by weight. The following abbreviations are used:
EA: ethyl acrylate
MA: methyl acrylate
HQME: hydroquinone methyl ester Examples 1 to 4

A double-jacketed reactor supplied with oil at 80° C. and surmounted by a distillation column with Multiknit packing (efficiency: 15 theoretical plates), with a condenser at the top of the column supplied with oil at 50° C. and a dry-ice trap, is charged with:
  500 g or 550 g of fraction to be treated (containing 40% of EA; 59.5% of ethanol; acetaldehyde; diethoxyethane)
  0 or 50 g of Lewatit K1461 or Amberlyst 15 resin
  0 or 50 g of water
  0.1% HQME
  the total weight of the fraction to be treated+water being equal to 550 g.

Bubbling with low-oxygen air at 8% $O_2$ (vol.) is maintained throughout the test (3 hours).

It is heated to boiling at 63° C., removing the acetaldehyde by distillation as it forms.

The contents of acetaldehyde and of diethoxyethane are determined by gas chromatography.

|  | Type of resin | Water, g | Fraction to be treated, g | Weight after treatment, g | Acetaldehyde content, ppm initial | Acetaldehyde content, ppm final | Diethoxyethane content, ppm initial | Diethoxyethane content, ppm final |
| --- | --- | --- | --- | --- | --- | --- | --- | --- |
| Ex 1 | None | 50 | 500 | 450 | 333 | 20 | 319 | 303 |
| Ex 2 | K1461 | 50 | 500 | 385 | 364 | 23 | 297 | 18 |
| Ex 3 | A15 | 50 | 500 | 400 | 303 | 12 | 319 | 10 |
| Ex 4 | K1461 | 0 | 550 | 430 | 383 | 56 | 356 | 264 |

It can be seen that in the absence of acid catalyst or in the absence of water, the diethoxyethane is not transformed to acetaldehyde and is therefore difficult to remove by distillation. The degree of removal of acetaldehyde by distillation is in nearly all cases greater than 90%.

Example 5

The preceding mixture from example 2 (500 g of fraction to be treated and 50 g of water) is treated in a stirred reactor heated by a double jacket provided with recirculation on a cartridge containing 200 ml of LEWATIT K1461 resin. The reactor is surmounted by a column with Multiknit packing of efficiency equal to 20 theoretical plates equipped with a condenser supplied with water at 30° C.

The mixture is fed into the reactor at a flow rate of 1500 g/h.

The acetaldehyde is distilled at the top of column at about 30 g/h. The composition of the overhead product is as follows:
EA: 28%
Ethanol: 66%
Acetaldehyde: 0.06%
The final mixture contains:
EA: 40%

Ethanol: 59.5%
Diethoxyethane: 180 ppm

The degree of removal of potential diethoxyethane in the mixture before treatment is greater than 90%.

Example 6

Referring to FIG. 1

The following azeotropic mixture containing:
EA: 40%
Ethanol: 60%
Acetaldehyde: 0.023%
Diethoxyethane: 0.05%
is distilled on a column C0 packed with 1" Pall rings with the following characteristics: diameter 32 cm; height 5 m; efficiency 10 theoretical plates.

The temperature at the condenser is about 30° C. The column is also equipped with a trap at −10° C.

The mixture is supplied to plate 4 of the column (counting from the top) at a flow rate of 1425 kg/h.

The overhead product containing acetaldehyde distils at 74° C. at atmospheric pressure at 4 kg/h.

Its composition by weight is as follows:
EA: 27.7%
Ethanol: 65%
Acetaldehyde: 7.3%
Diethoxyethane: 0.02%
A mixture composed of:
EA: 40%
Ethanol: 60%
Acetaldehyde: 3 ppm
Diethoxyethane: 0.05%
is recovered at the bottom.

The overhead product, which corresponds to 0.3% of the initial mixture, is removed, which represents a very low loss of EA and a rate of recovery of acetaldehyde of 90%.

The bottom product, depleted of acetaldehyde, the major contributor to the introduction of diethoxyethane in the EA unit via recycling, can be recycled to this unit.

Example 7

Referring to FIG. 2

A stirred, heated reactor R1, surmounted by a distillation column C packed with 2 beds of 3 and 5 m and having 15 theoretical plates, is charged with the following mixture (7745 kg/h):
EA: 29.7%
DMAE: 13.8%
DMAEA: 37%
EtOH: 12.4%
Acetaldehyde: 44 ppm
Heavy fractions: 5%

The temperature of the condenser is about 30° C. and that of the vent trap −8° C.

The pressure at the top of column is 650 mmHg.

The acetaldehyde-rich fraction is distilled at the top of the column whereas the purified azeotrope is withdrawn at theoretical plate 7 (counting from the condenser). This gives an ethanol purity above 66% and removes more than 90% of the acetaldehyde present.

The head leakage (1 kg/h) consists of:
Acetaldehyde: 21.2%
EA: 23.5%
Ethanol: 54.8%

The side stream (1217 kg/h) consists of:
EA: 33.9%
Ethanol: 66%
Acetaldehyde: 0.0014%

Example 8

Referring to FIG. 3

Column C3 (at plate 7 from the bottom) is supplied at 800 kg/h with a stream 3 having the following composition by weight:
EA: 17%
Ethanol: 74%
Water: 8%
Acetaldehyde: 2800 ppm The column operates in the following conditions:
P: 2 bar—T° head: 65° C.—T° foot: 79° C.—column efficiency: 11 theoretical plates—reflux rate: 12/1.

We obtain:
a top stream 4a: 17 kg/h, consisting of:
EA: 47%
Ethanol: 35%
Water: 5%
Acetaldehyde: 13%
a bottom stream 4: 783 kg/h, consisting of
EA: 16.1%
Ethanol: 75.7%
Water: 8.2%

Example 9

Referring to FIG. 4

The stream fed to column C2 at a rate of 349.3 kg/h has the following composition by weight:
EA: 5.8%
Ethanol: 21.9%
Water: 72.1%
Acetaldehyde: 1500 ppm (0.52 kg/h)

The feed to column C3 takes place at plate 6. The efficiency of this column is 7 theoretical plates.

The purge at the top of column C3 is 1 kg/h. It is deliberately limited so as not to lose too much EA and ethanol.

The mass flow rate of acetaldehyde purged at the top of column C3 is 476 g/h.

The mass flow rate of acetaldehyde returned to the reaction is 44 g/h, i.e. a degree of reduction of the amount of acetaldehyde in the plant of 91.5%.

The invention claimed is:

1. A method for purifying an azeotropic fraction generated during the synthesis of N,N-dimethyl aminoethyl acrylate of formula:

$$H_2C=CHCOOCH_2CH_2N(CH_3)_2$$

by transesterification of an alkyl acrylate of formula $CH_2=CH—COOR_1$ by N,N-dimethyl aminoethanol,
wherein $R_1$ represents a methyl or ethyl radical;
said method comprising:
distilling transesterification reaction products in a first distillation column in communication with a transesterification reactor to yield an azeotropic fraction comprising:
an alkyl acrylate,
a lower alcohol, $R_1OH$, formed during the reaction, and
by-products comprising acetaldehyde and dialkoxyethane of formula $CH_3CH(OR_1)_2$;

(a) distilling the azeotropic fraction in a second distillation column to yield:
- a minority acetaldehyde-rich overhead product comprising alkyl acrylate, lower alcohol, most of the acetaldehyde, and traces of the dialkoxyethane, and
- a low-acetaldehyde main fraction comprising alkyl acrylate, lower alcohol, most of the dialkoxyethane, and traces of the acetaldehyde;

removing said acetaldehyde-rich product, and
recovering said low-acetaldehyde main fraction at the bottom of the second column; or (b) distilling the azeotropic fraction directly in the first distillation column,
removing the acetaldehyde-rich product, and
drawing off the low-acetaldehyde main fraction via a side stream from the first column; and recycling the low-acetaldehyde fraction to a synthesis process for alkyl acrylate comprising reaction of acrylic acid and lower alcohol.

2. The method of claim 1, wherein the azeotropic fraction is distilled directly in the first distillation column.

3. The method of claim 1, wherein the azeotropic fraction is distilled in a second distillation column.

4. The method of claim 3, wherein the azeotropic fraction is treated with water in the presence of an acid catalyst to convert the dialkoxyethane to acetaldehyde and lower alcohol, and
the acetaldehyde is distilled as it forms.

5. The method of claim 3, further comprising:
washing the azeotropic fraction with water and distilling the azeotropic fraction in an extraction column to yield:
- a bottom aqueous fraction comprising most of the water, the lower alcohol, and acetaldehyde, and
- a top fraction comprising alkyl acrylate and dialkoxyethane;

recycling the top fraction directly to the transesterification reaction, and
distilling the aqueous fraction to yield a fraction that is depleted of acetaldehyde and rich in lower alcohol.

6. The method of claim 5, further comprising:
distilling the bottom aqueous fraction in a distillation column to yield a bottom fraction comprising water and an overhead fraction comprising lower alcohol and acetaldehyde;
removing or recycling the water to the extraction column with the azeotropic fraction;
distilling the overhead fraction in a separate distillation column to remove a top acetaldehyde fraction and yield a bottom low-acetaldehyde alcohol fraction; and
recycling the alcohol fraction to react with acrylic acid.

7. The method of claim 6, wherein part of the bottom alcohol fraction is recycled to react with acrylic acid and part of the bottom alcohol fraction is recycled to the overhead fraction comprising lower alcohol and acetaldehyde.

8. The method of claim 6, further comprising:
recycling most of the top acetaldehyde fraction to reflux the separate distillation column and
purging the remainder of the top acetaldehyde fraction to lower the concentration of acetaldehyde.

9. The method of claim 5, wherein washing the azeotropic fraction with water is carried out directly in a production unit for alkyl acrylate at a step for purification of the raw acrylate obtained from an acrylic acid/alcohol reaction mixture, said washing step comprising:
introducing the azeotropic fraction into a liquid/liquid extraction column integrated in a plant for production of alkyl acrylate,
wherein the liquid/liquid extraction column is supplied with water and a raw reaction mixture after removal of a proportion of the water from the reaction, heavy compounds and residual acrylic acid.

10. A method for synthesis of N,N-dimethyl aminoethyl acrylate of formula:

$$H_2C=CHCOOCH_2CH_2N(CH_3)_2$$

comprising:
transesterifying an alkyl acrylate of formula $CH_2=CH—COOR_1$ with N,N-dimethyl aminoethanol,
wherein $R_1$ comprises a methyl or ethyl radical;
purifying an azeotropic fraction generated during the transesterification step,
wherein said purifying step comprises:
distilling the azeotropic fraction in a distillation column to yield:
- a minority acetaldehyde-rich overhead product comprising alkyl acrylate, lower alcohol, most of the acetaldehyde, and traces of the dialkoxyethane, and
- a low-acetaldehyde main fraction comprising alkyl acrylate, lower alcohol, most of the dialkoxyethane, and traces of the acetaldehyde, removing said acetaldehyde-rich product, and
recovering said low-acetaldehyde main fraction; and.
recycling the low-acetaldehyde main fraction to an alkyl acrylate production unit.

11. A method for purifying an azeotropic fraction comprising:
(i) reacting alkyl acrylate of formula $CH_2=CH—COOR_1$ with N,N-dimethyl aminoethanol to yield reaction products comprising N,N-dimethyl aminoethyl acrylate, wherein $R_1$ represents a methyl or ethyl radical;
(ii) distilling the reaction products to yield an azeotropic fraction comprising:
alkyl acrylate,
$R_1OH$,
acetaldehyde, and
$CH_3CH(OR_1)_2$;
(iii) distilling the azeotropic fraction to yield:
an acetaldehyde-rich fraction and
a low-acetaldehyde fraction;
(iv) reacting $R_1OH$ in the low-acetaldehyde fraction with acrylic acid to yield alkyl acrylate; and
(v) recycling the alkyl acrylate product of step (iv) to the reaction of step (i).

* * * * *